United States Patent [19]

Saari

[11] Patent Number: 4,794,266

[45] Date of Patent: Dec. 27, 1988

[54] METHOD AND APPARATUS FOR LIGHT TRANSMISSION MEASUREMENT BY SENDING LIGHT, MEASURING RECEIVED LIGHT AND COMPUTING TRANSMITTANCE

[75] Inventor: Heikki Saari, Espoo, Finland

[73] Assignee: Vaisala Oy, Helsinki, Finland

[21] Appl. No.: 10,766

[22] Filed: Feb. 4, 1987

[30] Foreign Application Priority Data

Feb. 4, 1986 [FI] Finland ............................... 860499

[51] Int. Cl.⁴ ..................... G01N 15/06; G01N 15/07
[52] U.S. Cl. ................................. 250/573; 250/227; 356/437
[58] Field of Search ............... 250/573, 227; 356/436, 356/437, 438, 439; 350/96.1

[56] References Cited

U.S. PATENT DOCUMENTS

| | | | |
|---|---|---|---|
| 3,308,709 | 3/1967 | Harrick | 350/96.1 |
| 4,040,749 | 8/1977 | David et al. | 356/437 |
| 4,676,638 | 6/1987 | Yasuda | 250/573 |

FOREIGN PATENT DOCUMENTS 2420594 11/1975 Fed. Rep. of Germany ...... 356/436
1242621 3/1968 United Kingdom .

Primary Examiner—David C. Nelms
Assistant Examiner—William L. Oen
Attorney, Agent, or Firm—Birch, Stewart, Kolasch & Birch

[57] ABSTRACT

Measurement equipment based on the measurement of light transmission are plagued by changing characteristics of protective glass surfaces due to contamination or other factors. In a method, light transmission is measured by sending light from a transmitter (1) and recording the received light intensity at a receiver (2), after which the light intensity is obtained by computation means. Light from light sources (5, 6) travels into protective glasses (3, 4) of the transmitter and the receiver so that the light rays are subjected to total internal reflection within the glasses, after which the intensities of the totally reflected light rays are measured by a detector (7, 8), and the obtained intensity values are used for correcting the intensity attenuation, effected by the protective glasses and their contamination onto the path from the transmitter to the receiver. The apparatus comprises light sources (5, 6) integral with the transmitter (1) and the receiver (2), with the light rays from the light sources adapted to enter the protective glasses in such a manner as to be subjected to a total internal reflection, and detectors (7, 8) for intensity measurement of the totally reflected light rays.

8 Claims, 1 Drawing Sheet

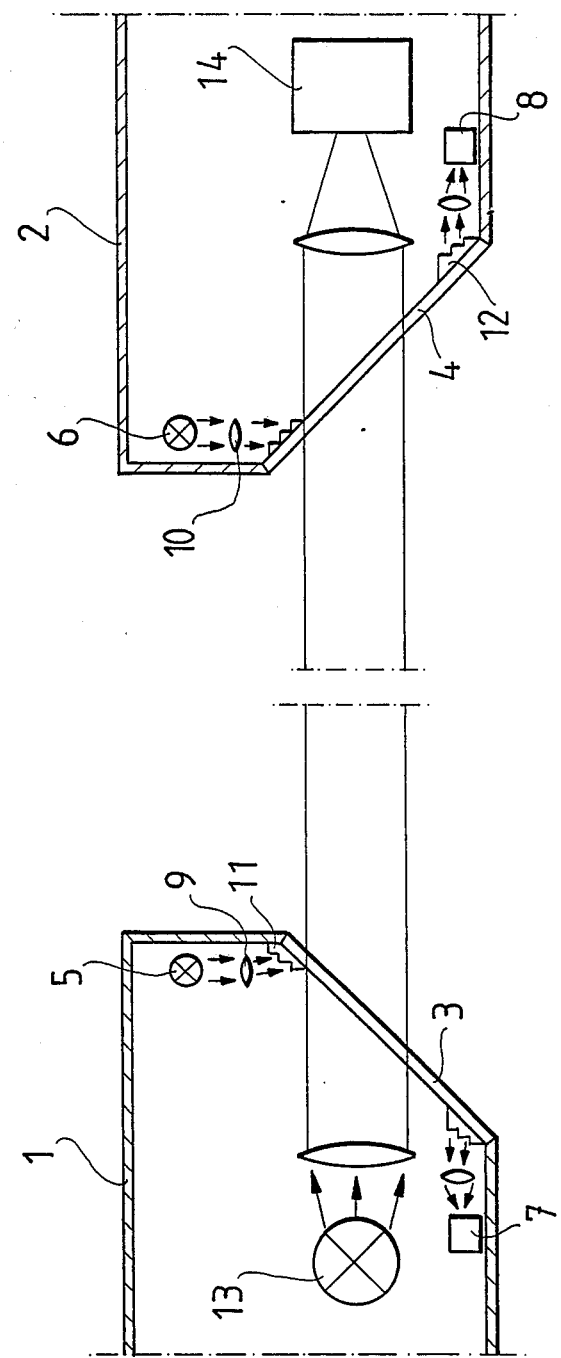

METHOD AND APPARATUS FOR LIGHT TRANSMISSION MEASUREMENT BY SENDING LIGHT, MEASURING RECEIVED LIGHT AND COMPUTING TRANSMITTANCE

BACKGROUND OF THE INVENTION

The present invention relates to a method for the measurement of light transmission, with the method based on sending light from a transmitter and measuring the received light intensity at a receiver, separated by a distance from the transmitter, and computing the transmittance. In addition, the invention concerns an apparatus for the implementation of the method.

DESCRIPTION OF THE PRIOR ART

Measurement equipment based on the transmission of light are utilized for recording visibility, and different types of equipment are used in various locations where exact information on visibility is needed, including, e.g. airfields and weather stations. The measurement is based on noting that the intensity result I measured at the receiver is directly proportional to the light transmission T through a medium as given by the formula $T = K \cdot I$, where K is a coefficient of proportionality, dependent on the medium. The measurements are plagued by the contamination and scratching of transmitter and receiver protective glasses, together with the time-related changes in their characteristics. These factors cause an error in the results of transmission measurements through a medium by inducing attenuation to the light beam transmitted through the protective glasses. Alleviation of the problem has been sought by the scheduled cleaning of the protective glasses, and by taking into account the possible changes of transmission in the calculations, as well as by replacement of the protective glasses. However, these operations are inconvenient, time consuming, and expensive to perform.

SUMMARY OF THE INVENTION

The invention aims to provide a method for the measurement of light transmission, with the method being capable of overcoming disadvantages involved with the conventional methods. In addition, the invention aims to provide a method in which changes in transmission due to changes in protective glass characteristics are taken into account in the measurements. Furthermore, the invention aims to provide an apparatus for the implementation of the method with an easy and reliable operation of the apparatus.

The goal of the invention is achieved by a method for measurement of light transmission and an apparatus therefore.

In the method according to the invention, light from the light sources is launched into the protective glasses of the transmitter and the receiver so as to obtain a total internal reflection within the glasses. The intensities of the totally reflected light beams are measured by means of detectors, and the obtained intensity values are utilized for correcting the light intensity attenuation on the path from the transmitter to the receiver, caused by the protective glasses and their contamination. The intensities of the totally reflected light rays are dependent on the contamination, scratches, and the like changes of the glass surfaces, causing attenuation on the transmitted light. Correspondingly, these contaminations, scratches, and the like cause attenuation to the light passing through the glass. The method in accordance with the invention uses attenuation of reflected light for the detection of the transmitted light attenuation and changes in the same. Dependence of the measurement values on the operating conditions may be extracted by performing observations which reveal the causes of transmission attenuation related to the scratches, contamination, aging, and the like factors of the protective glasses.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The invention is illustrated in the following in detail with reference to the enclosed drawing which illustrates in a diagrammatic side view an exemplifying embodiment of an apparatus in accordance with the present invention and which is not limitative of the present invention.

DETAILED DESCRIPTION OF THE PREFERRED EMBODIMENTS

The apparatus shown in the FIGURE comprises a transmitter 1 and a receiver 2 spaced at a distance from the transmitter. A light source 5 is located in the vicinity of a protective glass 3 of the transmitter, a collimator 9 is located between the light source and the protective glass, a prism matrix 11 is located on the surface of the protective glass, and the other end of the protective glass is provided with another prism matrix and a detector 7. The collimator is adapted to collimate the light emitted from the light source and to direct the light towards the prism matrix. This application uses the prism matrix for guiding the light into the protective glass so as to obtain a total internal reflection from the walls of the glass, whereas other conventional optical means for the same purpose are also applicable. The light emitted by the light source is guided into the protective glass to obtain a total internal reflection from the walls of the protective glass, after which the light is guided out from the glass, and the light intensity is measured by means of a detector.

Correspondingly, located in the vicinity of a protective glass 4, the receiver has a light source 6, a collimator 10, prism matrices 12, and a detector 8, members which are located and operate in a similar manner as illustrated in the foregoing.

The transmitter is provided with a light source 13 and the receiver is provided with a detector 14.

When the protective glasses are clean, the apparatus shown in the figure correctly measures the light transmission T in a medium, and the intensity measurement result I of the detector 14 is directly proportional to the transmission as given by the formula $T = K \cdot I$.

A measurement error caused by the changes in the transmitter and receiver protective glass characteristics can be corrected by means of intensity measurements of light rays with a total internal reflection within the protective glasses. The detector 7 measures the intensity $I_1$ of light rays with the total internal reflection within the transmitter protective glass, and the detector 8 measures the intensity $I_2$ of light rays with the total internal reflection within the receiver protective glass. When both protective glasses are contaminated, the measured intensities are $I'$, $I_1'$, and $I_2'$. When the transmitter protective glass is cleaned, the measured intensities are $I''$, $I_1$, and $I_2'$. When both the transmitter and receiver protective glasses are cleaned, the intensities are I, $I_1$, and $I_2$.

The following differences are denoted:

$$T_1 = (I'' - I')/I', \qquad T_2 = (I - I')/I$$

$$R_1 = (I_1 - I_1')/I_1, \qquad R_2 = (I_2 - I_2')/I_2$$

where $T_1$ is the change in the transmitted light intensity caused by the contamination of the transmitter protective glass, $R_1$ is the change in the intensity of the totally reflected light rays in the transmitter proctective glass caused by the contamination of the glass, $T_2$ is the change in the transmitted light intensity caused by the contamination of the receiver protective glass, and $R_2$ is the change in the intensity of the totally reflected light rays in the receiver protective glass caused by the contamination of the glass.

When the protective glasses are cleaned, new pairs of values $(T_1, R_1)$ and $(T_2, R_2)$ are always obtained. Based on these pairs of values, function tables $T_1 = f_1(I_1)$ and $T_2 = f_2(I_2)$ can be obtained. After a sufficient number of protective glass cleaning and intensity measurement cycles, with the aid of the functions $f_1$ and $f_2$, the results of transmission measurements through a medium can be corrected for the effect of errors caused by the contamination of protective glasses by means of the following formula:

$$T = \frac{K \cdot I}{(1 - f_1(I_1)) \cdot (1 - f_2(I_2))}$$

where
K = coefficient of proportionality
I = received intensity at detector 14
$I_1$ = received intensity at detector 7
$I_2$ = received intensity at detector 8

The functions $f_1$ and $f_2$ depend on the circumstances in which the protective glasses are placed and on the geometry of the measurement configuration for the totally reflected light. By standardizing the geometry of the measurement configuration, the functions $f_1$ and $f_2$ can be predetermined on the basis of measurement results if the results are obtained in circumstances corresponding to those in which the apparatus will be used. If the measurement results are not recorded in the operating conditions, the functions $f_1$ and $f_2$ are selected to correspond to the closest results available and they are corrected by help of measurements performed in conjunction with cleaning operations.

In the apparatus shown in the FIGURE, the protective glasses of the transmitter and the receiver are inclined downward. Consequently, loose dirt will not adhere to the surfaces of the protective glasses where it might influence the measurement but will fall off.

When more than a single transmission measurement apparatus is available, and the distances from the transmitter to the receivers in the system are different, the method in accordance with the invention can be used for determining the correct transmission value for a receiver with a shorter distance by means of the measurement result of the receiver with the longest distance if the transmission through the medium is sufficiently high. In this case, the correct transmission values of the receiver with the shorter distance can be used for automatic correction of the functions $f_1$ and $f_2$.

The invention is not limited to the illustrated embodiment but can be varied within the scope of the claims presented. Such variations are not to be regarded as a departure from the spirit and scope of the invention, and all such modifications as would be obvious to one skilled in the art are intended to be included within the scope of the following claims.

What is claimed is:

1. A method for measurement of light transmission comprising the steps of:
   sending light from a transmitter through a first protective glass;
   receiving the light through a second protective glass at least at one receiver, said receiver being located at a distance from said transmitter;
   measuring an intensity value of the light received by said at least one receiver;
   calculating a preliminary transmission value by using the intensity value;
   transmitting light through both the first and second protective glasses to obtain a total internal reflection inside the first and second protective glasses;
   measuring the intensities of both of the lights totally reflected inside the first and second protective glasses by detectors; and
   calculating and correcting attenuations of the totally reflected lights caused by the first and second protective glasses and their contamination by using the intensities of both of the lights in order to calculate a final transmission value.

2. The method as recited in claim 1, further comprising the steps of:
   receiving light at least at two receivers located at different distances from the transmitter; and
   using measurement results from the receiver located farthest from the transmitter to determine a correct light intensity for the receiver located closer to the transmitter.

3. The method as recited in claim 1, further comprising the steps of:
   measuring the intensity value of the light received by said at least one receiver and the intensity values of both of the totally reflected lights when the first and second protective glasses are clean;
   measuring the intensity value of the light received by said at least one receiver and the intensity values of both of the totally reflected lights when said first and second protective glasses are dirty;
   measuring the intensity value of the light received by said at least one receiver and the intensity values of both of the totally reflected lights when one of the first and second protective glasses is clean and the other one is dirty; and
   determining a transmission value correction coefficient based on the intensity values from said measuring of clean, dirty and combination of clean and dirty protective glasses.

4. The method as recited in claim 1, further comprising the steps of:
   aligning light rays of the light transmitted through both the first and second protective glasses by collimators located between light sources and the protective glasses whereby the light rays meet the protective glasses at an angle to obtain a total internal reflection inside the glasses; and launching the light into the protective glasses and thereafter, guiding the light from the protective glasses to detectors by using optical devices.

5. An apparatus for measurement of light transmission comprising:

a transmitter having a first protective glass, said transmitter emitting light through said first protective glass;

at least one receiver located a distance from the transmitter, said at least one receiver having a second protective glass through with the light emitted from the transmitter passes;

means for measuring an intensity value of the light received by said at least one receiver;

a first light source within said first protective glass to obtain a total internal reflection of said light;

a second light source within said receiver for transmitting light through said second protective glass to obtain a total internal reflection of said light;

a first detector within said transmitter for receiving and measuring the intensities of the totally reflected light;

a second detector within said receiver for receiving and measuring the intensities of the totally reflected light; and means for calculating and correcting attenuation of the totally reflected lights caused by the first and second protective glasses and their contamination by using the intensities of both of the lights in order to calculate a final transmission value.

6. The apparatus for measurement of light as recited in claim 5, wherein said first and second protective glasses are each inclined for avoiding adhering by certain contaminants.

7. The apparatus for measurement of light as recited in claim 5, further comprising:

at least one collimator for said transmitter, said collimator being located between the first light source and the light protective glass and at least another collimator for said receiver, said another collimator being located between the second light source and the second protective glass, said collimators aligning light rays of light transmitted from said first and second light sources in order for said rays to meet the protective glasses at an angle to obtain a total internal reflection inside the glasses; and optical means for launching the light into the protective glasses and thereafter guiding the light from the protective glasses to said detectors, said optical means being provided for both said transmitter and said receiver and being located at sides of the protective glasses.

8. The apparatus for measurement of light as recited in claim 5, further comprising:

at least a second receiver located at a distance from said transmitter different from the distance the first receiver is located from said transmitter;

second means for measuring at least an intensity value of light received at said second receiver; and means for calculating a correct light intensity for the first receiver using at least the intensity value of light measured by said second means for measuring.

* * * * *